US00PP33070P2

(12) United States Plant Patent
Mendoza et al.

(10) Patent No.: US PP33,070 P2
(45) Date of Patent: May 18, 2021

(54) STRAWBERRY PLANT VARIETY NAMED 'DRISSTRAWEIGHTYTWO'

(50) Latin Name: ***Fragaria* x *ananassa***
Varietal Denomination: DrisStrawEightyTwo

(71) Applicant: Driscoll's, Inc., Watsonville, CA (US)

(72) Inventors: Omar Carrillo Mendoza, Watsonville, CA (US); Xiomara Ruiz Ruiz, Watsonville, CA (US); Philip J. Stewart, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/912,523

(22) Filed: Jun. 25, 2020

(51) Int. Cl.
*A01H 6/74* (2018.01)
*A01H 5/08* (2018.01)

(52) U.S. Cl.
USPC ..... Plt./209

(58) Field of Classification Search
USPC ..... Plt./209
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson, Jr. et al.
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 Lopez
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP19,767 P2 2/2009 Shaw et al.
PP20,248 P3 9/2009 Rogers et al.
PP20,363 P2 9/2009 Chandler
PP20,701 P2 2/2010 Gilford et al.
PP20,731 P2 2/2010 Mowrey et al.
PP20,733 P2 2/2010 Mowrey et al.

(Continued)

OTHER PUBLICATIONS

Stewart, et al., "Unpublished U.S. Appl. No. 16/873,276, filed Mar. 10, 2020, titled"Strawberry Plant Variety Named 'Dris-StrawEighty'.
Stewart, et al., "Unpublished U.S. Appl. No. 16/873,277, filed Mar. 10, 2020, titled"Strawberry Plant Variety Named 'Dris-StrawEightyOne'.
Mendoza, et al., "Unpublished U.S. Appl. No. 16/912,629, filed Jun. 25, 2020, titled"Strawberry Plant Variety Named 'Dris-StrawEightyThree'.
Ferguson et al., "Unpublished U.S. Appl. No. 16/501,428, filed Apr. 12, 2019, titled "Strawberry Plant Variety Named 'Dris-StrawSeventyFive'"".
Ferguson et al., "Unpublished U.S. Appl. No. 16/501,759, filed Jun. 4, 2019, titled "Strawberry Plant Variety Named 'Dris-StrawSeventySeven'"".

(Continued)

*Primary Examiner* — Annette H Para
(74) *Attorney, Agent, or Firm* — Morrison & Foerster LLP

(57) ABSTRACT

A new and distinct variety of strawberry plant named 'DrisStrawEightyTwo', particularly selected for its high early season and total yield when grown at high elevation, the size, flavor, and shelf-life of its fruit, as well as its tolerance to mites and easy-to-harvest plant architecture, is disclosed.

5 Drawing Sheets

(56) References Cited

U.S. PATENT DOCUMENTS

| | | | |
|---|---|---|---|
| PP20,735 | P2 | 2/2010 | Ferguson |
| PP20,775 | P2 | 2/2010 | Mowrey et al. |
| PP20,922 | P2 | 4/2010 | Gilford et al. |
| PP21,538 | P2 | 11/2010 | Gilford et al. |
| PP21,559 | P2 | 12/2010 | Ferguson et al. |
| PP21,762 | P2 | 3/2011 | Stewart et al. |
| PP22,040 | P3 | 7/2011 | Stewart et al. |
| PP22,218 | P2 | 11/2011 | Ferguson et al. |
| PP22,247 | P2 | 11/2011 | Ferguson |
| PP23,107 | P2 | 10/2012 | Ferguson et al. |
| PP23,148 | P2 | 10/2012 | Gilford et al. |
| PP23,377 | P2 | 2/2013 | Ferguson et al. |
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| PP29,289 | P3 | 5/2018 | Vitten et al. |
| PP29,728 | P2 | 10/2018 | Stewart et al. |
| PP29,729 | P2 | 10/2018 | Kibbe et al. |
| PP29,730 | P2 | 10/2018 | Kibbe et al. |
| PP29,731 | P2 | 10/2018 | Ferguson et al. |
| PP29,747 | P2 | 10/2018 | Vitten et al. |
| PP29,748 | P2 | 10/2018 | Vitten et al. |
| PP29,749 | P2 | 10/2018 | Stewart et al. |
| PP30,775 | P2 | 8/2019 | Carrillo Mendoza et al. |
| PP30,789 | P2 | 8/2019 | Ferguson et al. |
| PP30,818 | P2 | 8/2019 | Pakozdi et al. |
| PP30,851 | P2 | 8/2019 | Fear et al. |
| PP30,936 | P2 | 10/2019 | Stewart et al. |
| PP31,083 | P2 | 11/2019 | Carrillo Mendoza et al. |
| PP31,233 | P2 | 12/2019 | Pakozdi et al. |
| PP31,527 | P3 | 3/2020 | Carrillo Mendoza et al. |
| PP31,655 | P2 | 4/2020 | Carrillo Mendoza et al. |
| PP31,703 | P2 | 4/2020 | Stewart et al. |
| PP31,827 | P2 | 6/2020 | Ferguson et al. |
| PP31,896 | P2 | 6/2020 | Pakozdi et al. |
| 2003/0079263 | P1 | 4/2003 | Gilford et al. |
| 2013/0276182 | P1 | 10/2013 | Fear et al. |

OTHER PUBLICATIONS

Ferguson et al., Unpublished U.S. Appl. No. 16/602,701, filed Nov. 22, 2019, titled "Strawberry Plant Variety Named Dris-StrawSixtyNine".

Jacobs et al., "Unpublished U.S. Appl. No. 16/501,501, filed Apr. 18, 2019, titled "Strawverry Plant Variety Named 'Dris-StrawSeventy'"".

Mendoza et al., "Unpublished U.S. Appl. No. 16/350,139, filed Oct. 2, 2018, titled "Strawberry Plant Variety Named 'Dris-StrawSixtySeven'"".

Mendoza,"U.S. Unpublished U.S. Appl. No. 16/501,602, filed May 7, 2019, titled "Strawberry Plant Variety Named 'Dris-StrawSixtyEight'"".

Mendoza et al., "Unpublished U.S. Appl. No. 16/501,849, filed Jun. 18, 2019, titled "Strawberry Plant Variety Named 'Dris-StrawSeventyEight'"".

Mendoza et al., Unpublished U.S. Appl. No. 16/602,476, filed Oct. 15, 2019, titled "Strawberry Plant Variety Named Dris-StrawSeventyNine".

Pakozdi et al., "Unpublished U.S. Appl. No. 16/501,198, filed Mar. 5, 2019, titled "Strawberry Plant Variety Named 'Dris-StrawSeventyThree'"".

Stewart et al., "Unpublished U.S. Appl. No. 16/501,449, filed Apr. 17, 2019, titled "Strawberry Plant Variety Named 'Dris-StrawSeventyOne'"".

STRAWBERRY PLANT VARIETY NAMED 'DRISSTRAWEIGHTYTWO'

Latin name:

Botanical classification: *Fragaria* x *ananassa.*

Varietal denomination: The varietal denomination of the claimed variety of strawberry plant is 'DrisStrawEightyTwo'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawEightyTwo'.

Strawberry plant variety 'DrisStrawEightyTwo' originated from a cross between the proprietary female parent '920AA240' (unpatented) and the proprietary male parent '914U 19' (unpatented). Progeny plants from this cross of '920AA240' x '914U 19', including 'DrisStrawEightyTwo', were asexually propagated via stolons in Zapotlan, Jalisco, Mexico in March of 2014. Strawberry plant variety 'DrisStrawEightyTwo' was later specifically identified and selected in Tangancicuaro, Michoacan, Mexico in December of 2014.

'DrisStrawEightyTwo' was subsequently asexually propagated via stolons, and underwent further testing at test plots in Tapalpa, Jalisco, Mexico and Purepero, Michoacan, Mexico for five years (2014 to 2019). The present variety has been found to be stable and reproduce true to type through successive asexual propagations via stolons and tissue culture.

'DrisStrawEightyTwo' exhibits the following distinguishing characteristics when grown under normal horticultural practices in Tapalpa, Jalisco, Mexico and Purepero, Michoacan, Mexico:

1. Obtuse shape of base of terminal leaflet;
2. Medium glossiness of fruit;
3. Absent or small fruit cavity; and
4. Position of achenes level with surface on fruit.

'DrisStrawEightyTwo' was particularly selected for its high early season and total yield when grown at high elevation, the size, flavor, and shelf-life of its fruit, as well as its tolerance to mites and easy-to-harvest plant architecture.

DESCRIPTION OF THE DRAWINGS

This new strawberry plant is illustrated by the accompanying photographs which show fruit of the plant, flowers, leaves, and the plants. The colors shown are as true as can be reasonably obtained by conventional photographic procedures. The photographs are of plants that are six months old.

DETAILED BOTANICAL DESCRIPTION

Figure 1:
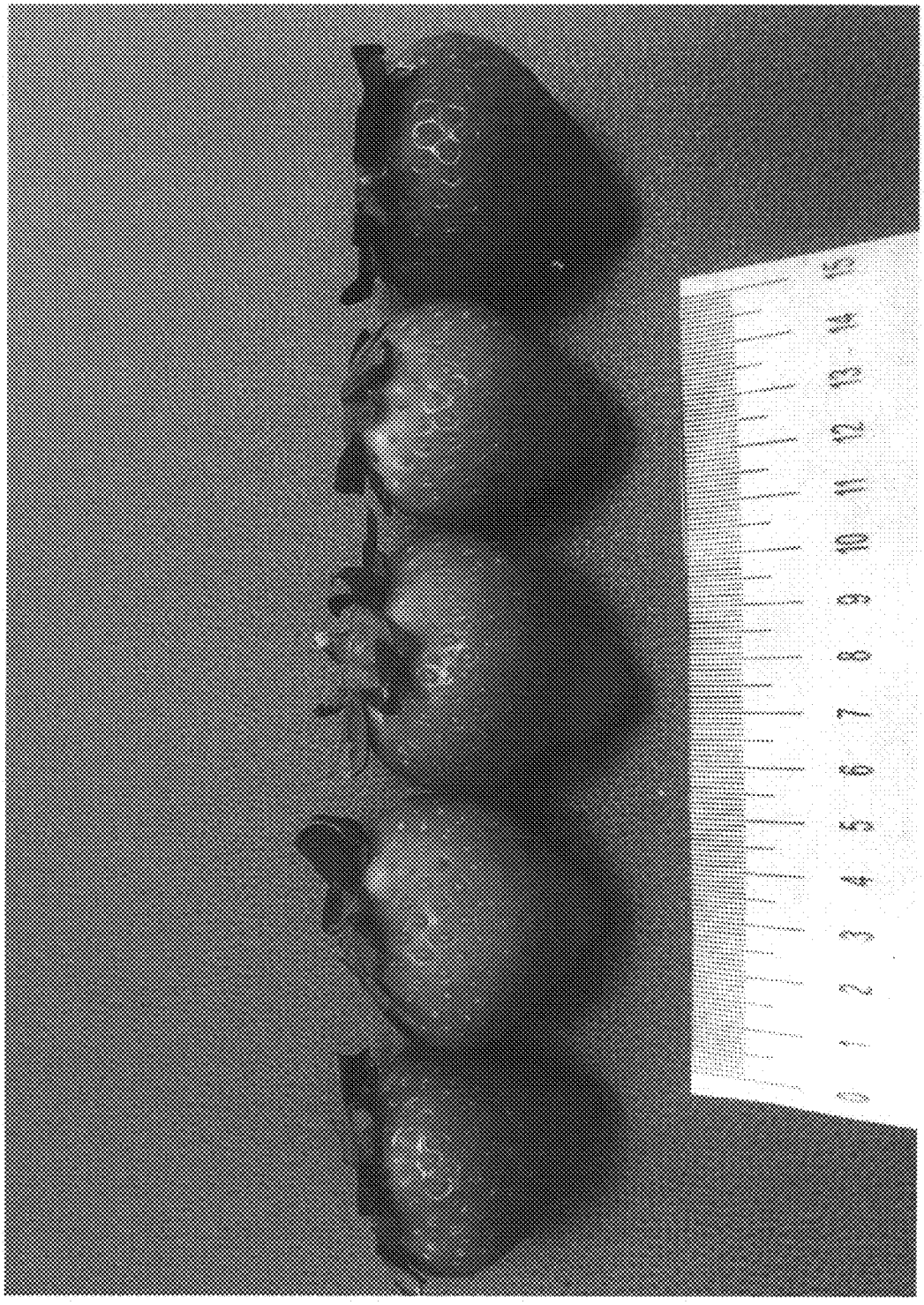
FIG. 1 illustrates whole fruit of variety 'DrisStrawEightyTwo'.
Figure 2:
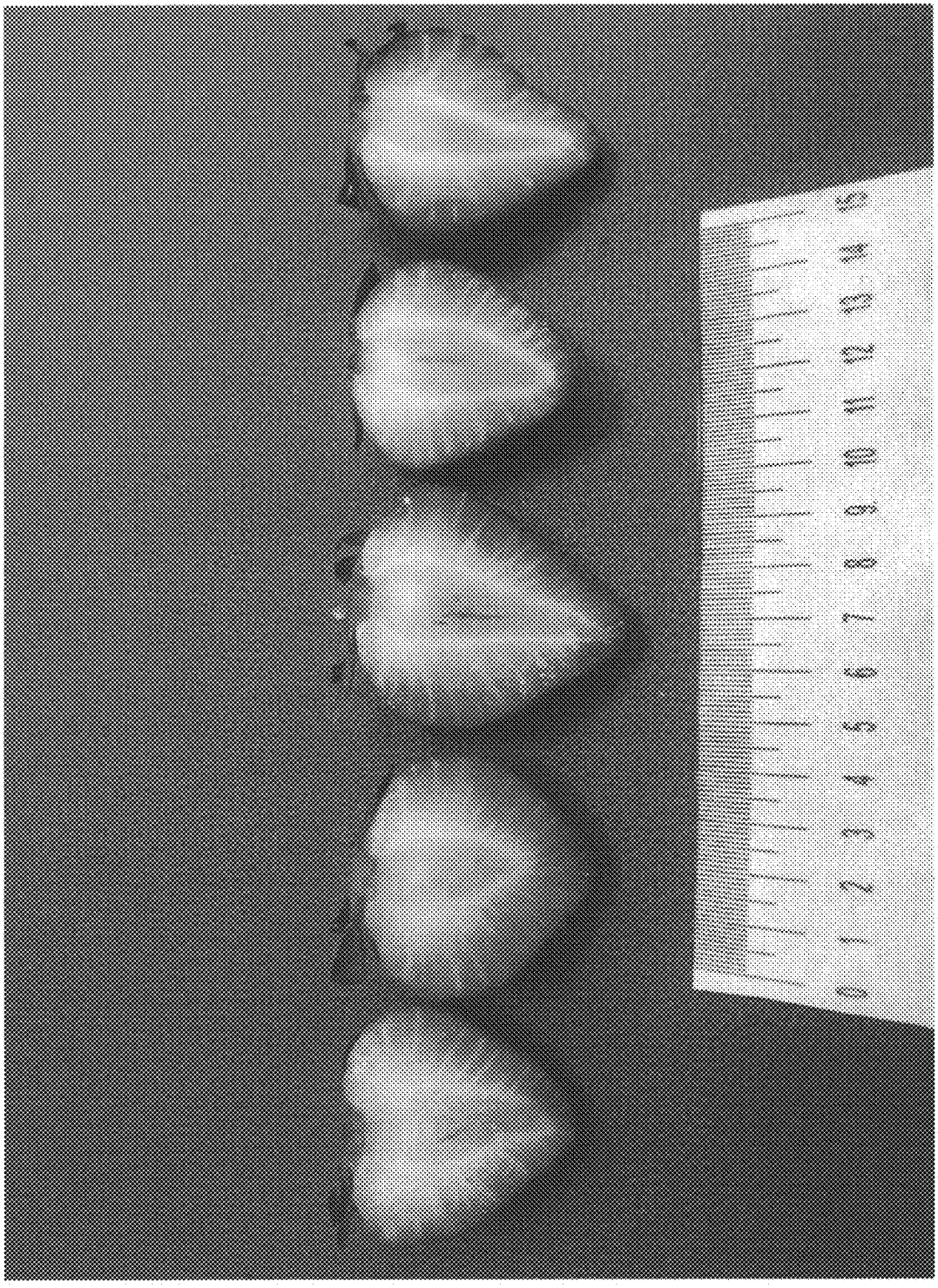
FIG. 2 illustrates longitudinal sections of fruit of variety 'DrisStrawEightyTwo'.
Figure 3:
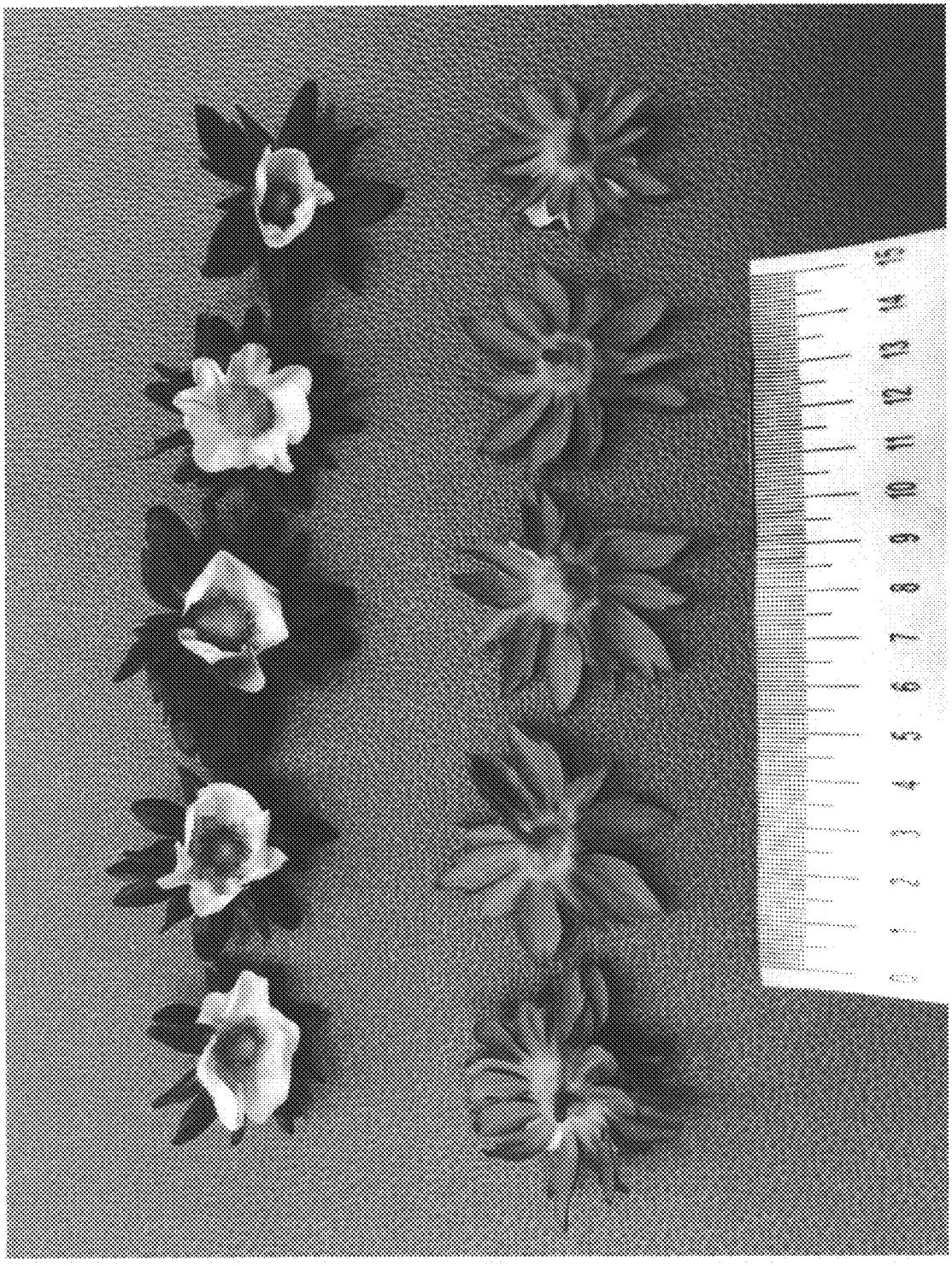
FIG. 3 illustrates the upper and lower surfaces of flowers of variety 'DrisStrawEightyTwo'.
Figure 4:
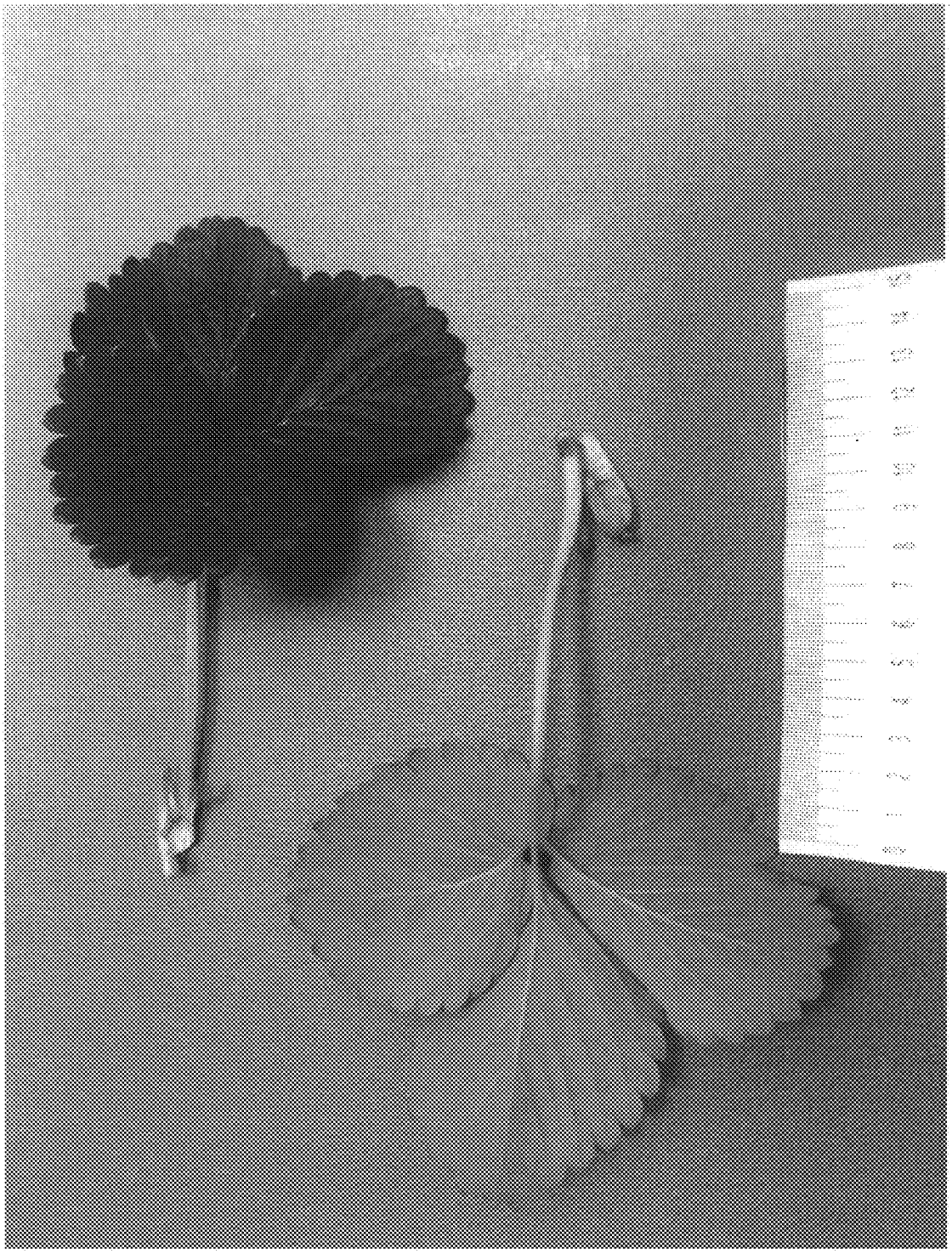
FIG. 4 illustrates leaves of variety 'DrisStrawEightyTwo'.
Figure 5:
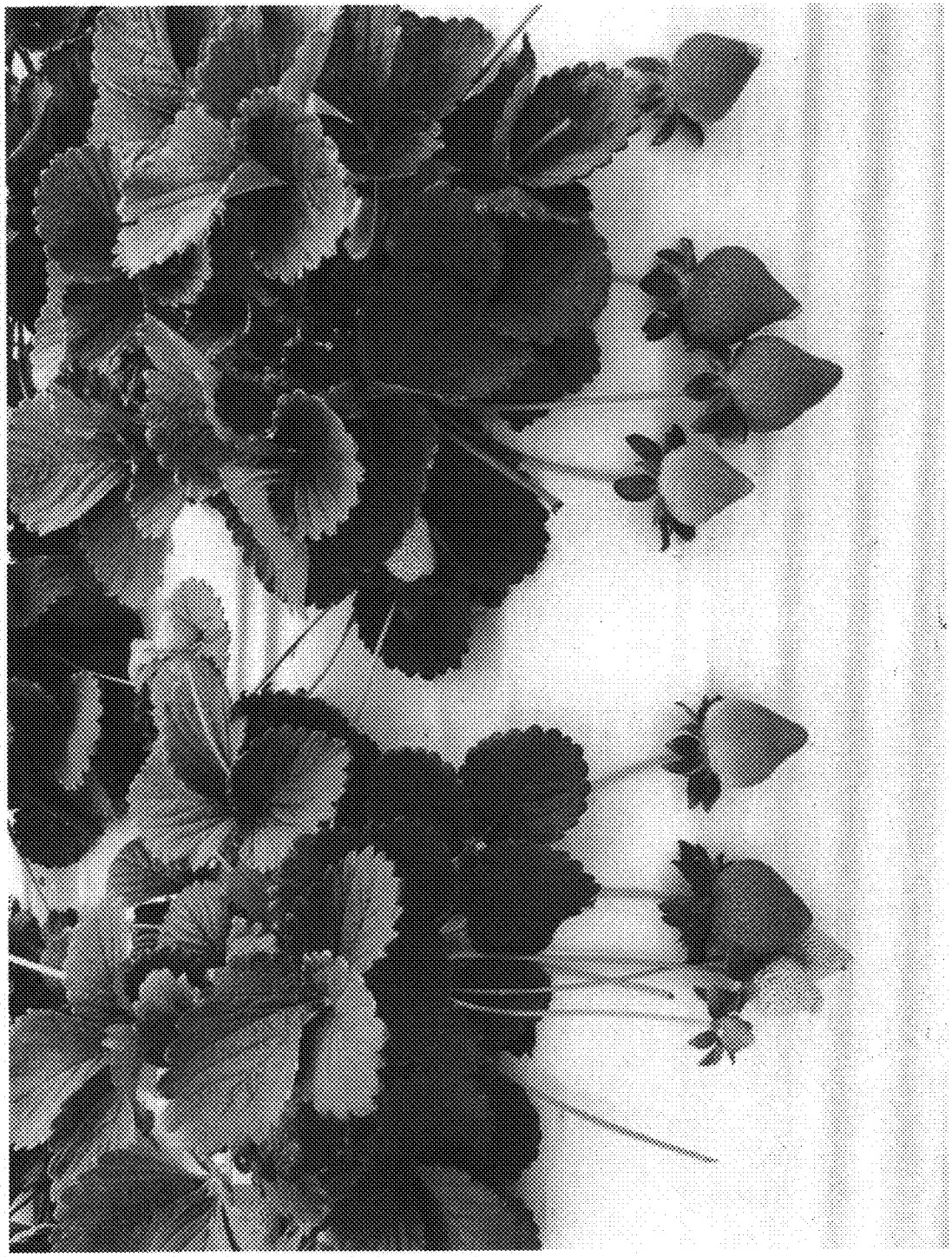
FIG. 5 illustrates whole plants of variety 'DrisStrawEightyTwo'.

The following detailed descriptions set forth the distinctive characteristics of 'DrisStrawEightyTwo'. The data which define these characteristics is based on observations taken in Tapalpa, Jalisco, Mexico and Purepero, Michoacan, Mexico from 2014 to 2019. This description is in accordance with UPOV terminology. Color designations, color descriptions, and other phenotypical descriptions may deviate from the stated values and descriptions depending upon variation in environmental, seasonal, climatic, and cultural conditions. 'DrisStrawEightyTwo' has not been observed under all possible environmental conditions. The botanical description of 'DrisStrawEightyTwo' was taken from plants that were six months old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Species.*—*Fragaria* x *ananassa.*

*Common name.*—Strawberry.

*Denomination.*—'DrisStrawEightyTwo'.

Parentage:

*Female parent.*—Proprietary strawberry plant '920AA240' (unpatented).

*Male parent.*—Proprietary strawberry plant '914U 19' (unpatented).

Plant:

*Height.*—19.8 cm.

*Diameter.*—35.1 cm.

*Number of crowns per plant.*—2.4.

*Growth habit.*—Semi-upright.

Stolon:

*Average number of daughter plants per square foot.*—10.

*Diameter at bract.*—3.5 mm.
*Anthocyanin coloration.*—Medium.
*Stolon color with anthocyanin coloration.*—RHS 44C (Vivid reddish-orange).

Leaf:
*Number of leaflets.*—Three only.
*Color of upper surface.*—RHS NN137A (Greyish olive green).
*Variegation.*—Absent.
*Terminal leaflet.*—Length: 11 cm. Width: 15.2 cm. Length/width ratio: 0.7. Number of teeth/terminal leaflet: 21. Shape of base: Obtuse. Margin: Serrate to crenate. Shape in cross section: Straight.
*Petiole.*—Length: 12.8 cm. Diameter: 3.3 mm. Attitude of hairs: Slightly outwards. Bract frequency (number present on each petiole): 2.
*Petiolule.*—Length: 12 mm. Diameter: 1.6 mm.
*Stipule.*—Length: 3.0 cm. Width: 10.8 mm. Anthocyanin coloration: Medium. Anthocyanin color: RHS 42C (Strong reddish orange).

Inflorescence:
*Position in relation to foliage.*—Above.
*Pedicel.*—Attitude of hairs: Slightly outwards.
*Flower.*—Flower diameter (petal tip to petal tip on non-flattened flower): 27.9 mm. Arrangement of petals: Touching. Stamen: Present. Typical and observed number of flowers per plant: 12.3.
*Petal.*—Length: 13.6 mm. Width: 13.6 mm. Length/width ratio: 1.0. Typical and observed petal number: 5.8. Color of upper side: RHS NN155C (White).
*Calyx.*—Diameter (sepal tip to sepal tip, measured on back of flower): 47.6 mm.
*Sepal.*—Length (sepal tip to point of attachment to receptacle): 22.1 mm. Width: 10.5 mm. Typical and observed sepal number: 13.

Fruit:
*Length.*—47 mm.
*Width.*—41 mm.
*Length/width ratio.*—1.1.
*Fruit hollow length.*—2.6 mm.
*Fruit hollow width.*—1.0 mm.
*Fruit hollow length/width ratio.*—2.6.
*Shape.*—Conical.
*Glossiness.*—Medium.
*Firmness.*—Medium.
*Color.*—RHS 45A (Vivid red).
*Position of achenes.*—Level with surface.
*Position of calyx attachment.*—Level with fruit.
*Attitude of sepals.*—Outwards.
*Color of flesh* (*excluding core*).—RHS 34C (Strong reddish orange).
*Color of core.*—RHS 31A (Strong reddish orange).

Production:
*Flowering interval.*—September to May.
*Harvest interval.*—October to May.
*Type of bearing.*—Fully remontant.
*Productivity.*—39,911 kg to 52,552 kg of fruit per hectare per season from six-month-old plants when grown in Tapalpa, Jalisco, Mexico.

Resistance to abiotic stress, pests, and diseases:
*Heat.*—Moderately resistant.
*Two-spotted spider mite* (*tetranychus urticae*).—Moderately resistant.
*Botrytis fruit rot* (*botrytis cinerea*).—Moderately resistant.
*Powdery mildew* (*podosphaera macularis*): Moderately resistant.
*Xanthomonas* (*xanthomonas fragariae*): Moderately susceptible.

COMPARISON WITH PARENTAL AND COMMERCIAL VARIETIES

'DrisStrawEightyTwo' differs from the proprietary female parent '920AA240' (unpatented) in that 'DrisStrawEightyTwo' has earlier fruit production and a more compact plant than '920AA240'.

'DrisStrawEightyTwo' differs from the proprietary male parent '914U 19' (unpatented) in that fruit of 'DrisStrawEightyTwo' are softer, more conic in shape, and larger in size than fruit of '914U 19'.

'DrisStrawEightyTwo' differs from the commercial variety 'Driscoll El Dorado' (U.S. Plant Pat. No. 16,238) in that 'DrisStrawEightyTwo' has an obtuse shape of base of terminal leaflet, a medium glossiness of fruit, an absent or small fruit cavity, and a level with surface position of achenes on fruit, whereas 'Driscoll El Dorado' has a rounded shape of base of terminal leaflet, a strong glossiness of fruit, a medium fruit cavity, and a below surface position of achenes on fruit. Further, 'DrisStrawEightyTwo' is fully remontant, while 'Driscoll El Dorado' is partially remontant.

'DrisStrawEightyTwo' differs from the commercial variety 'DrisStrawThirtySix' (U.S. Plant Pat. No. 25,698) in that 'DrisStrawEightyTwo' has an obtuse shape of base of terminal leaflet, a medium glossiness of fruit, an absent or small fruit cavity, and a level with surface position of achenes on fruit, whereas 'DrisStrawThirtySix' has an acute shape of base of terminal leaflet, a strong glossiness of fruit, a medium fruit cavity, and a below surface position of achenes on fruit. Further, 'DrisStrawEightyTwo' is fully remontant, while 'DrisStrawThirtySix' is not remontant.

We claim:

1. A new and distinct variety of strawberry plant named 'DrisStrawEightyTwo' as shown and described herein.

* * * * *